United States Patent
Nakamori

(10) Patent No.: US 10,371,448 B2
(45) Date of Patent: Aug. 6, 2019

(54) SAMPLE HEATING APPARATUS

(71) Applicant: SHIMADZU CORPORATION, Kyoto-shi, Kyoto (JP)

(72) Inventor: Akioki Nakamori, Nakagyo-ku (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/867,844

(22) Filed: Jan. 11, 2018

(65) Prior Publication Data
US 2018/0202717 A1    Jul. 19, 2018

(30) Foreign Application Priority Data
Jan. 17, 2017 (JP) .................. 2017-005618

(51) Int. Cl.
F27D 5/00 (2006.01)
F27D 3/00 (2006.01)
(Continued)

(52) U.S. Cl.
CPC ........... F27D 3/003 (2013.01); F27D 1/1858 (2013.01); G01N 1/44 (2013.01); G01N 35/04 (2013.01); F27D 2003/0059 (2013.01); G01N 2001/002 (2013.01); G01N 2001/2229 (2013.01); G01N 2035/00356 (2013.01); G01N 2035/042 (2013.01)

(58) Field of Classification Search
CPC .... F27D 2003/0059; F27D 5/00; F27D 19/00; C21D 9/00; F27B 9/22; F27B 1/20; F27B 5/12; F27B 7/32
See application file for complete search history.

(56) References Cited

U.S. PATENT DOCUMENTS 8,926,251 B2 * 1/2015 Iizuka ............... H01L 21/67389
                                                      414/217
9,240,311 B2 * 1/2016 Whitehouse ........ H01J 49/0413
(Continued)

FOREIGN PATENT DOCUMENTS

JP    2014-115172 A    6/2014
JP    2015081784 A     4/2015

OTHER PUBLICATIONS

Communication dated Jun. 20, 2018, from the European Patent Office in counterpart European Application No. 18151997.6.
(Continued)

Primary Examiner — Gregory A Wilson
(74) Attorney, Agent, or Firm — Sughrue Mion, PLLC

(57) ABSTRACT

A sample heating device includes: an opening/closing cover provided to be movable in a horizontal direction between a position above an opening of a mounting port and a position displaced from the position above the opening, and a cover sliding mechanism that is engaged with a part of a sample boat conveying portion when the sample boat conveying portion comes to a predetermined position in a horizontal plane and moves the opening/closing cover in the horizontal direction according to upward and downward movements of the sample boat conveying portion so that the opening/closing cover is provided at the position directly above the opening of the mounting port when the sample boat conveying portion comes to a predetermined height.

5 Claims, 5 Drawing Sheets

(51) Int. Cl.
*F27D 1/18* (2006.01)
*G01N 1/44* (2006.01)
*G01N 35/04* (2006.01)
G01N 1/00 (2006.01)
G01N 1/22 (2006.01)
G01N 35/00 (2006.01)

(56) References Cited

U.S. PATENT DOCUMENTS

| | | | |
|---|---|---|---|
| 9,360,466 B2 * | 6/2016 | Iharada | G01N 33/1846 |
| 9,508,914 B2 * | 11/2016 | Ono | H01L 39/02 |
| 2012/0257949 A1 * | 10/2012 | Schmid | B66C 17/08 |
| | | | 414/172 |
| 2016/0011165 A1 | 1/2016 | Iharada | |
| 2018/0202718 A1 * | 7/2018 | Nakamori | F27B 9/22 |
| 2018/0211854 A1 * | 7/2018 | Hillman | H01L 21/67109 |

OTHER PUBLICATIONS

Communication dated Apr. 4, 2019, from State Intellectual Property Office of the P.R.C in counterpart application No. 201810038599.6.

* cited by examiner

SAMPLE HEATING APPARATUS

BACKGROUND OF THE INVENTION

1. Field of the Invention

The present invention relates to a sample heating device in which a sample rested in a sample boat is inserted into a heating furnace and heated.

2. Description of the Related Art

There is a known sample heating device in which a liquid or solid sample is rested in a sample boat, placed in a heating furnace, and subjected to heating treatment (see Japanese Patent Application Laid-Open No. 2014-115172). Such a sample heating device is used, for example, for measurement of carbon components in the sample.

The sample heating device includes the heating furnace that heats the sample, a mounting port to which the sample boat to be subjected to the heating treatment in the heating furnace is mounted, and a sample moving bar that introduces the sample boat mounted to the mounting port into the heating furnace. Carrier gas is supplied into the heating furnace, and components to be measured that are generated by heating of the sample in the heating furnace are introduced by the carrier gas into an analytical instrument.

A user of such a sample heating device opens a cover of the mounting port, mounts the sample boat to the mounting port, closes the cover of the mounting port, and then manually moves the sample moving bar to move the sample boat into the heating furnace. After the heating treatment is finished, the user manually moves the sample moving bar to move the sample boat to the mounting port, opens the cover of the mounting port, and takes out the sample boat.

As described above, in the prior-art sample heating device, the operations such as the mounting of the sample boat to the mounting port, the introduction of the sample boat into the heating furnace, and the taking out of the sample boat are carried out manually. To automate the operations, a mechanism for opening and closing the cover of the mounting port is required in addition to a mechanism for holding and conveying the sample boat.

SUMMARY OF THE INVENTION

Therefore, it is an object of the present invention to achieve a mechanism for automatically opening and closing the cover of the mounting port with a simple structure.

A sample heating device according to the present invention includes: a heating furnace that has within itself a space for housing a sample boat holding a sample to be heated and heats the sample held in the sample boat inserted into the space; a sample boat rack on which the sample boat is placed; a mounting port which communicates with the space inside the heating furnace and has an opening in an upper face and to which the sample boat to be subjected to heating treatment in the heating furnace is mounted through the opening; a sample boat introducing mechanism that introduces the sample boat mounted in the sample boat mounting portion into the heating furnace; a sample boat conveying portion that moves in a direction in a horizontal plane and a vertical direction, holds the sample boat placed on the sample boat rack, and mounts the sample boat to the mounting port; an opening/closing cover provided to be movable in a horizontal direction between a position above the opening of the mounting port and a position displaced from the position above the opening; and a cover sliding mechanism that is engaged with a part of the sample boat conveying portion when the sample boat conveying portion comes to a predetermined position in the horizontal plane and moves the opening/closing cover in the horizontal direction according to upward and downward movements of the sample boat conveying portion so that the opening/closing cover is provided at the position directly above the opening of the mounting port when the sample boat conveying portion comes to a predetermined height.

As the cover sliding mechanism, there is a mechanism including a guide rail that is attached to the opening/closing cover and inclined with respect to the vertical direction as a structure to be engaged with the part of the sample boat conveying portion, the part of the sample boat conveying portion being engaged with the guide rail and sliding along the guide rail when the sample boat conveying portion moves up and down to thereby move the opening/closing cover in the horizontal direction.

In the above-described case, a roller that can rotate in a vertical plane is preferably provided to the part of the sample boat conveying portion to be engaged with the guide rail. In this way, the part of the sample boat conveying portion smoothly slides along the guide rail, which allows the opening/closing cover to smoothly slide in the horizontal direction.

According to a preferred aspect of the invention, the guide rail is inclined in such a direction as to move the opening/closing cover toward the position above the opening of the mounting port according to the downward movement of the sample boat conveying portion and the sample heating device further includes an opening/closing cover pushing portion that moves up and down with the sample boat conveying portion and pushes the opening/closing cover from above in synchronization with the downward movement of the sample boat conveying portion so that the opening/closing cover coming to the position above the opening of the mounting port to seal the opening. In this way, it is possible to achieve a horizontal moving operation and a pushing operation of the opening/closing cover by utilizing the upward and downward movements of the sample boat conveying portion.

The sample heating device in the invention includes the opening/closing cover provided to be movable in the horizontal direction between the position above the opening of the mounting port and the position displaced from the position above the opening and the cover sliding mechanism that is engaged with the part of the sample boat conveying portion when the sample boat conveying portion comes to the predetermined position in the horizontal plane, moves the opening/closing cover in the horizontal direction according to the upward and downward movements of the sample boat conveying portion, and is provided at the position directly above the opening of the mounting port when the sample boat conveying portion reaches the predetermined height. Therefore, by utilizing the upward and downward movements of the sample boat conveying portion, it is possible to move the opening/closing cover in the horizontal direction between the position above the opening of the mounting port and the position displaced from the position above the opening. In this way, a drive portion for driving the opening/closing cover in the horizontal direction becomes unnecessary, which simplifies the device structure.

DETAILED DESCRIPTION OF THE INVENTION

An embodiment of a sample heating device will be described below by using the drawings.

Figure 1:
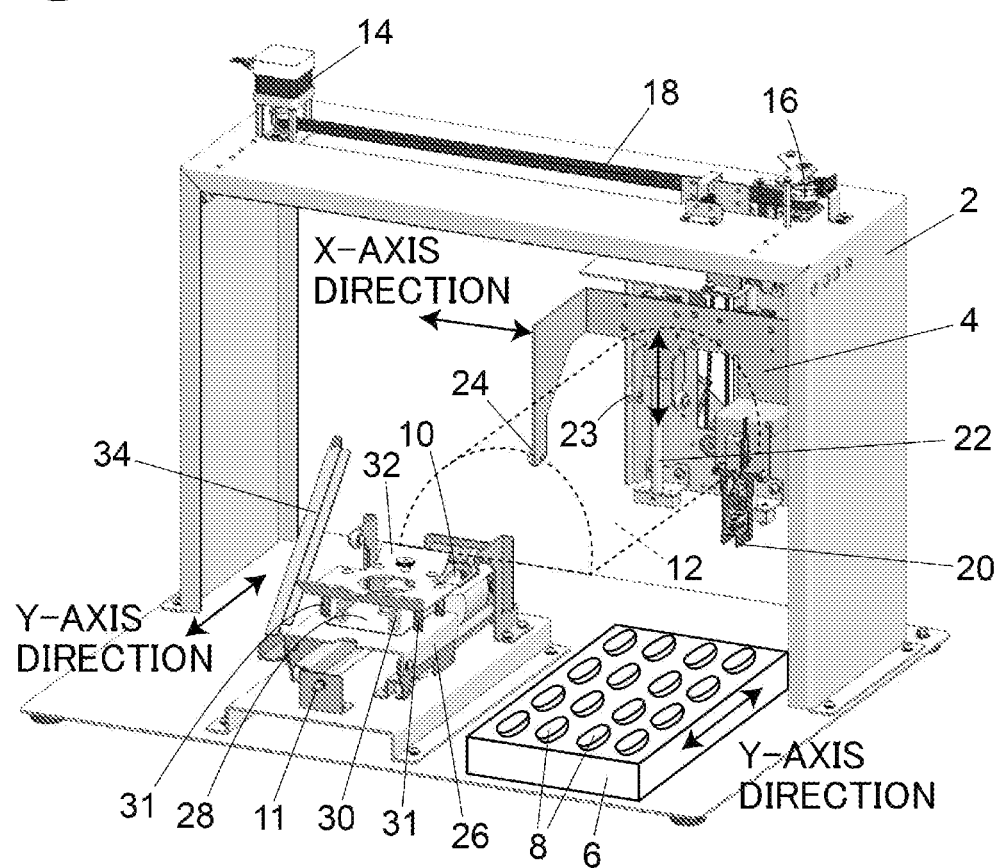
FIG. 1 is a perspective view schematically showing a structure of an embodiment of a sample heating device.

As shown in FIG. 1, the sample heating device of the embodiment includes an autosampler 2 having a function of automatically introducing a sample boat housing a sample to be analyzed into a heating furnace 12. In FIG. 1, the autosampler 2 is shown in solid lines and the heating furnace 12 is shown in broken lines.

The autosampler 2 mainly includes a sample boat conveying portion 4 that conveys a sample boat 8, a sample boat rack 6 on which the plurality of sample boats 8 are placed, and a mounting port 10 to which the sample boat 8 to be subjected to heating treatment in the heating furnace 12 is mounted.

The sample boat conveying portion 4 is formed to move in an X-axis direction which is one direction in a horizontal plane over the sample boat rack 6 and the mounting port 10. The sample boat conveying portion 4 is mounted to be movable to a guide rail (not shown) attached to a top panel of a housing of the autosampler 2 and extending in the X-axis direction. In the embodiment, a motor 14, a pulley 16, and a belt 18 are provided as a mechanism for moving the sample boat conveying portion 4. The motor 14 and the pulley 16 are attached to the top panel of the housing of the autosampler 2, and the belt 18 is stretched under tension between the motor 14 and the pulley 16. By driving the motor 14, the belt 18 moves, and the sample boat conveying portion 4 fixed to the belt 18 moves in the X-axis direction.

The sample boat conveying portion 4 includes a holding portion 20 that holds one sample boat 8 and a mechanism that moves the holding portion 20 vertically up and down. The holding portion 20 is moved vertically up and down along a vertical shaft 22 by the mechanism. The sample boat conveying portion 4 is provided with an opening/closing cover pushing portion 23 and a cover sliding roller 24. Both of the opening/closing cover pushing portion 23 and the cover sliding roller 24 are formed to move vertically up and down together with the holding portion 20. Details of the opening/closing cover pushing portion 23 and the cover sliding roller 24 will be described later.

The plurality of sample boats 8 are arranged and placed on the sample boat rack 6. Although it is not shown in detail in the drawing, the sample boat rack 6 is formed to move in a Y-axis direction orthogonal to the X-axis direction in the horizontal plane and can position a desired sample boat 8 under a moving path of the holding portion 20 of the sample boat conveying portion 4. In this way, the sample boat conveying portion 4 can hold the desired sample boat 8 out of the sample boats 8 placed on the sample boat rack 6 by using the holding portion 20.

The mounting port 10 is provided beside the sample boat rack 6 and under the moving path of the holding portion 20 of the sample boat conveying portion 4. In this way, the sample boat conveying portion 4 can hold the desired sample boat 8 on the sample boat rack 6 by using the holding portion 20 and mount the sample boat 8 to the mounting port 10.

Figure 2:
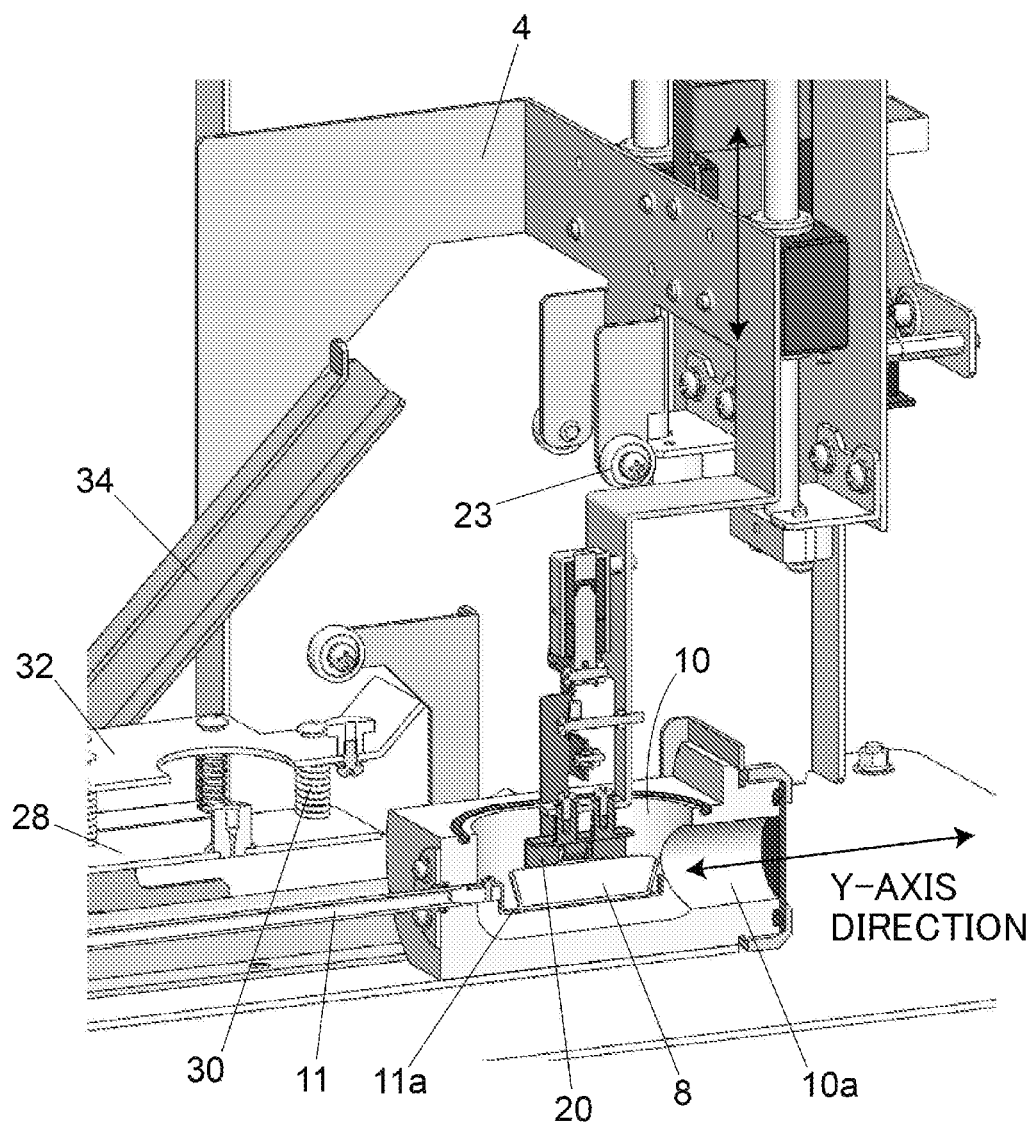
FIG. 2 is a sectional perspective view showing a structure around a mounting port of the embodiment.

The mounting port 10 has an open upper face and has within itself a space communicating with the heating furnace 12. A structure of the mounting port 10 will be described by using FIG. 2 together with FIG. 1. The mounting port 10 communicates with the heating furnace 12 through a sample boat passage 10a. Into the mounting port 10, a sample moving bar 11 extending in the Y-axis direction is inserted from a side of the mounting port 10 opposite from the heating furnace 12. The sample moving bar 11 is driven in the Y-axis direction by a mechanism (not shown) including a motor and the like. A sample boat resting portion 11a on which the sample boat 8 is rested is provided to a tip end portion of the sample moving bar 11. By driving the sample moving bar 11 in the Y-axis direction with the sample boat 8 rested on the sample boat resting portion 11a, the sample boat 8 is introduced into and taken out of the heating furnace 12.

Carrier gas is supplied into the space inside the mounting port 10 (not shown) and the carrier gas is introduced into an analytical instrument via the heating furnace 12, the analytical instrument connected to the heating furnace 12. The heating furnace 12 has within itself a space into which the sample boat 8 is introduced and performs the heating treatment for the sample boat 8 introduced into the space. Components to be analyzed that are generated from the sample as a result of the heating treatment for the sample boat 8 are introduced by the carrier gas supplied from a side of the mounting port 10 into the analytical instrument and analyzed.

Referring back to FIG. 1 to continue the description, an opening in the upper face of the mounting port 10 is opened and closed with an opening/closing cover 28 that slides in the Y-axis direction. A cover sliding mechanism that slides the opening/closing cover 28 in the Y-axis direction will be described below.

A cover retaining plate 32 is provided above the opening/closing cover 28. The cover retaining plate 32 is resiliently supported by a sliding base 26 by use of coil springs 31. The opening/closing cover 28 is held by the cover retaining plate 32 by use of coil springs 30. Instead of the coil springs 30 and 31, other resilient members such as flat springs may be used.

Figure 3:
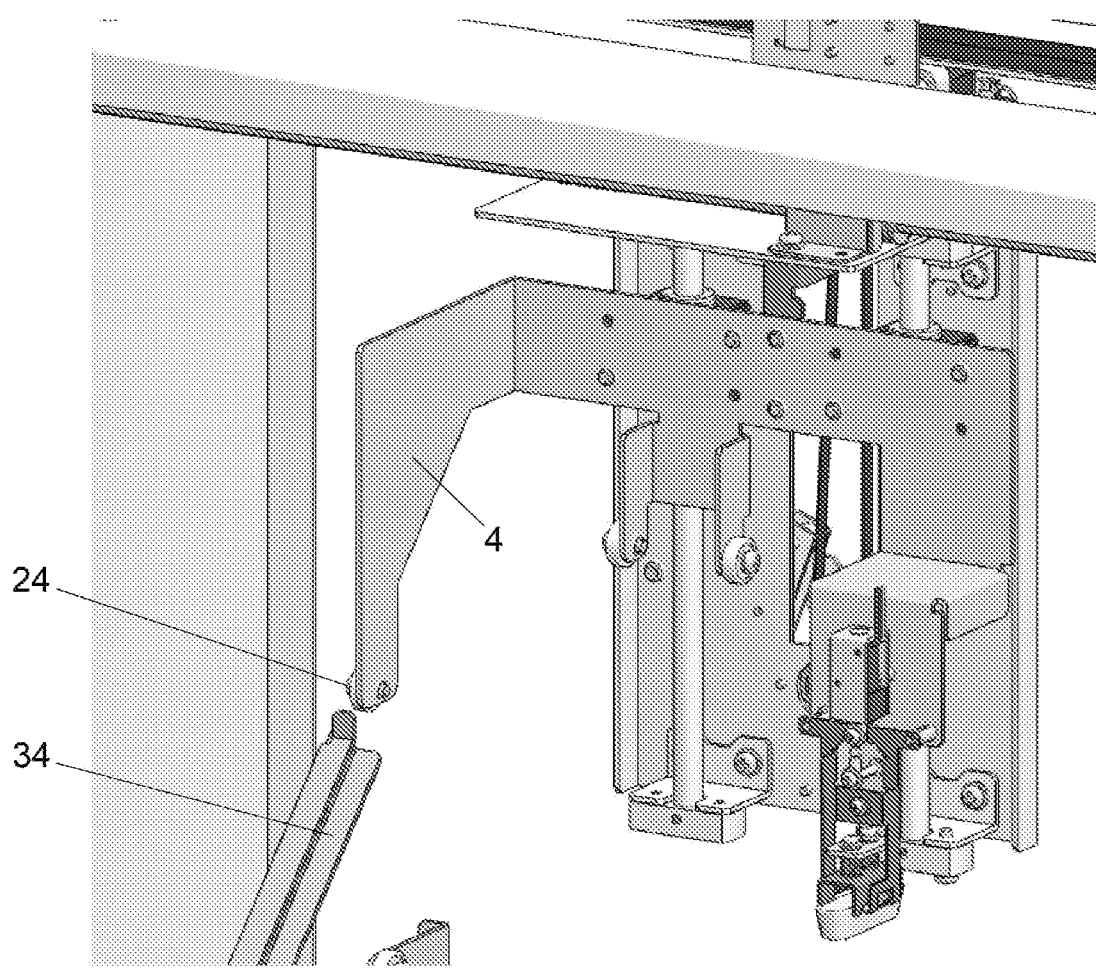
FIG. 3 is a sectional view for explaining a cover sliding mechanism of the embodiment.

A guide rail 34 is attached to the sliding base 26. As shown in FIG. 3, the guide rail 34 has an open upper end portion and the cover sliding roller 24 is fitted into the guide rail 34 through the opening to slide. A guide face of the guide rail 34 is inclined with respect to a vertical direction and the sliding base 26 slides in the Y-axis direction according to a vertical operation of the cover sliding roller 24 fitted in the guide rail 34. In other words, the guide rail 34 is for converting a vertical movement of the sample boat conveying portion 4 into a horizontal movement of the sliding base 26. The cover sliding roller 24 forms an engagement portion to be engaged with the guide rail 34.

Here, a position of the sample boat conveying portion 4 in the X-axis direction when the sample boat conveying portion 4 mounts the sample boat 8 to the mounting port 10 and a position of the sample boat conveying portion 4 in the X-axis direction when the cover sliding roller 24 of the sample boat conveying portion 4 is fitted into the guide rail 34 are different from each other.

Figure 4:
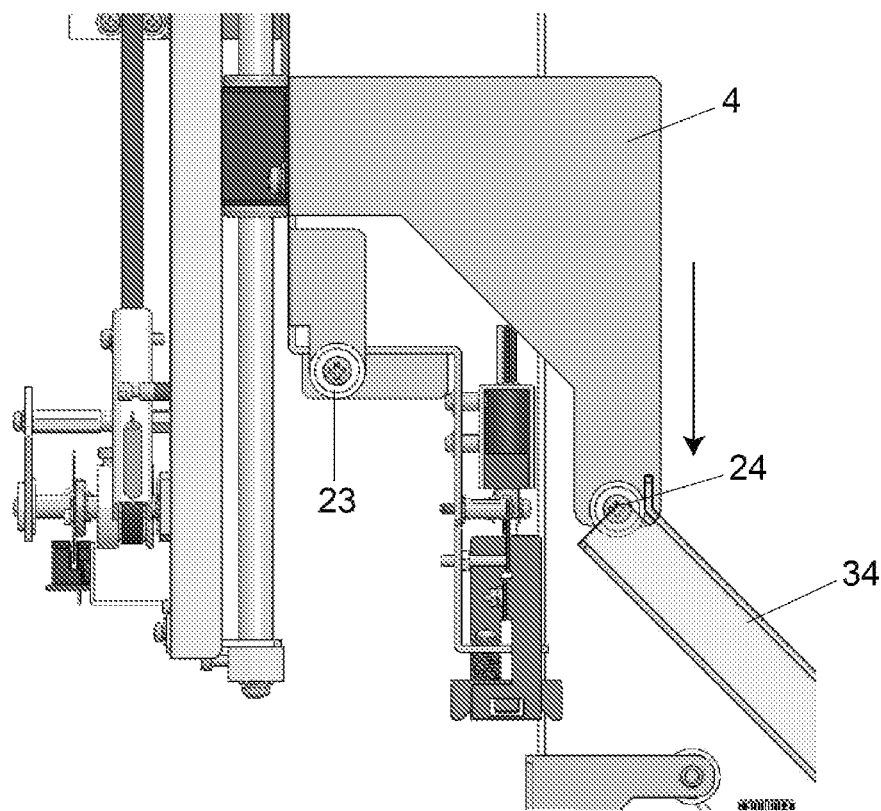
FIG. 4 is a side view showing a state before an opening/closing cover of the mounting port is closed by the cover sliding mechanism of the embodiment.
Figure 5:
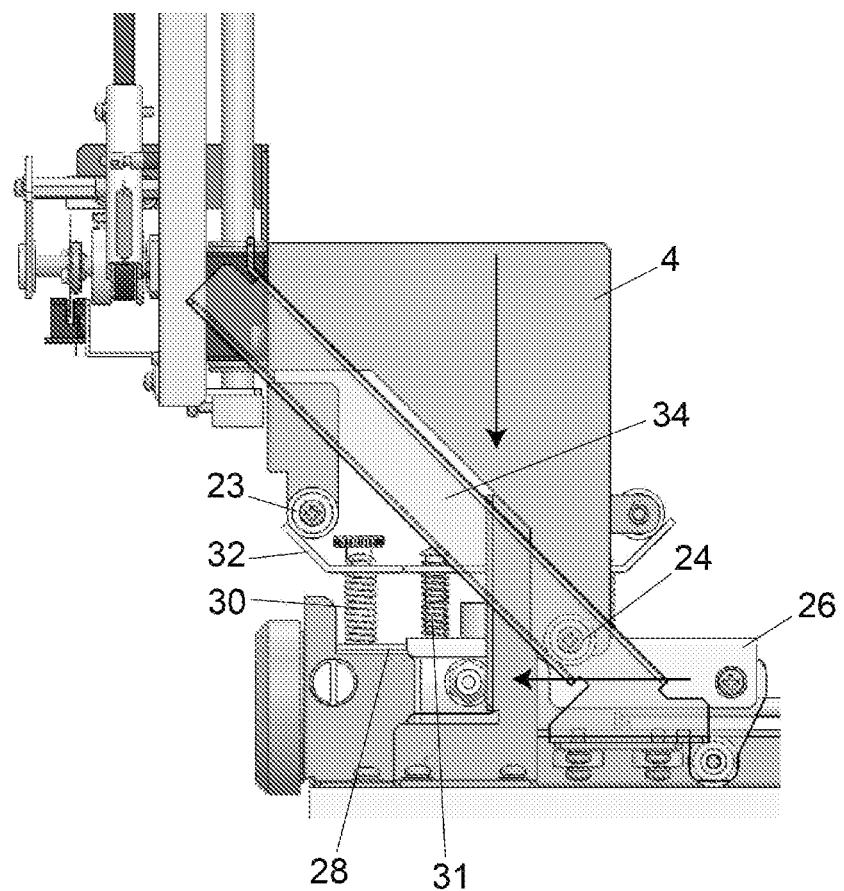
FIG. 5 is a side view showing a state in which the opening/closing cover of the mounting port is closed by the cover sliding mechanism of the embodiment.

In the embodiment, as shown in FIGS. 4 and 5, the guide face is inclined so as to move the sliding base 26 in a direction (leftward in FIGS. 4 and 5) for causing the opening/closing cover 28 to close the opening of the mounting port 10 when the sample boat conveying portion 4 moves down. When the sample boat conveying portion 4 moves down to a predetermined height, the opening/closing cover 28 comes to a position directly above the opening of the mounting port 10.

As shown in FIG. 5, when the sample boat conveying portion 4 moves down to a certain degree of height, the opening/closing cover pushing portion 23 comes in contact with the cover retaining plate 32. The height of the sample boat conveying portion 4 at this time is the height before the opening/closing cover 28 comes to the position directly above the opening of the mounting port 10. In the embodiment, tip ends of the opening/closing cover pushing portion 23 form rollers and do not obstruct sliding of the opening/closing cover pushing portion 23 in the Y-axis direction.

The opening/closing cover pushing portion 23 moves down as the sample boat conveying portion 4 moves down, and therefore pushes the cover retaining plate 32 downward from above. If the cover retaining plate 32 is pushed downward by the opening/closing cover pushing portion 23, the coil springs 30 between the opening/closing cover 28 and the cover retaining plate 32 contract into compressed states and resilient forces of the coil springs 30 push the opening/closing cover 28 downward. As a result, the opening/closing cover 28 is biased downward by the coil springs 30 at the position directly above the opening of the mounting port 10 to seal the opening of the mounting port 10.

An operation of the sample heating device of the embodiment will be described by using FIG. 1.

First, the sample boat conveying portion 4 holds one of the sample boats 8 on the sample boat rack 6 by using the holding portion 20 and conveys the sample boat 8 to the mounting port 10. At this time, the opening in the upper face of the mounting port 10 is open. The sample boat conveying portion 4 that has the sample boat 8 rested on the sample boat resting portion 11a (see FIG. 2) in the mounting port 10 then moves up to a predetermined position in the X-axis direction for engaging the cover sliding roller 24 with the guide rail 34.

After engaging the cover sliding roller 24 with the guide rail 34, the sample boat conveying portion 4 moves down, and the sliding base 26 moves in such a direction as to close the opening/closing cover 28 as the sample boat conveying portion 4 moves down. When the sample boat conveying portion 4 moves down to the certain degree of height, the opening/closing cover pushing portion 23 comes in contact with an upper face of the cover retaining plate 32. When the sample boat conveying portion 4 further moves down, the cover retaining plate 32 slides in the Y-axis direction while pushed downward. As a result, the opening/closing cover 28 reaches the position directly above the opening of the mounting port 10 while pushed downward by the cover retaining plate 32. In this way, the opening of the mounting port 10 is sealed.

After the opening of the mounting port 10 is sealed, the sample moving bar 11 is driven in the Y-axis direction to introduce the sample boat 8 rested on the sample boat resting portion 11a (see FIG. 2) of the sample moving bar 11 into the heating furnace 12 and the heating treatment for the sample boat 8 is started. At this time, the carrier gas is supplied into the heating furnace 12 from the side of the mounting port 10, and the components to be analyzed that are generated from the sample in the sample boat 8 are introduced by the carrier gas into the analytical instrument (not shown). Until the heating treatment is finished, the sample boat conveying portion 4 is on standby at the position where the sample boat conveying portion 4 closed the opening/closing cover 28.

After the heating treatment for the sample boat 8 is finished, the sample moving bar 11 is driven in the Y-axis direction to pull out the sample boat 8 from the heating furnace 12, and the sample boat 8 is cooled. After the cooling of the sample boat 8 is finished, the sample boat conveying portion 4 moves up to slide the sliding base 26 and the opening/closing cover 28 moves to a position displaced from the position directly above the opening of the mounting port 10. In this way, the mounting port 10 is opened.

Then, the sample boat conveying portion 4 holds the sample boat 8 in the mounting port 10 by using the holding portion 20, conveys the sample boat 8 to a predetermined disposal place (not shown), and disposes of the sample boat 8.

As described above, in the sample heating device of the embodiment, it is possible to slide the opening/closing cover 28 in the Y-axis direction by engaging the cover sliding roller 24 that is a part of the sample boat conveying portion 4 and the guide rail 34 with each other and moving the sample boat conveying portion 4 up and down, and therefore, a dedicated drive mechanism for sliding the opening/closing cover 28 in the horizontal direction is unnecessary.

Moreover, because the opening/closing cover pushing portion 23 comes in contact with the upper face of the cover retaining plate 32, and the opening/closing cover 28 held by the cover retaining plate 32 by use of the coil springs 30 is pushed downward when the sample boat conveying portion 4 moves down to the certain degree of height, it is possible to achieve both the sliding of the opening/closing cover 28 in the Y-axis direction and the downward pushing of the opening/closing cover 28 by only moving the sample boat conveying portion 4 up and down. In this way, the device structure becomes simple, which can suppress increase in footprint and cost.

What is claimed is:

1. A sample heating device comprising:
   a heating furnace that includes within itself a space for housing a sample boat holding a sample to be heated and heats the sample held in the sample boat inserted into the space;
   a sample boat rack on which the sample boat is placed;
   a mounting port which communicates with the space inside the heating furnace and has an opening in an upper face and to which the sample boat to be subjected to heating treatment in the heating furnace is mounted through the opening;
   a sample boat introducing mechanism that introduces the sample boat mounted in the mounting port into the heating furnace;
   a sample boat conveying portion that moves in a direction in a horizontal plane and a vertical direction, holds the sample boat placed on the sample boat rack, and mounts the sample boat to the mounting port;
   an opening/closing cover provided to be movable in a horizontal direction between a position above the opening of the mounting port and a position displaced from the position above the opening; and
   a cover sliding mechanism that is engaged with a part of the sample boat conveying portion when the sample boat conveying portion comes to a predetermined position in the horizontal plane and moves the opening/closing cover in the horizontal direction according to upward and downward movements of the sample boat conveying portion so that the opening/closing cover is provided at the position directly above the opening of the mounting port when the sample boat conveying portion comes to a predetermined height, wherein the cover sliding mechanism includes a guide rail that is attached to the opening/closing cover and inclined with respect to the vertical direction as a structure to be engaged with the part of the sample boat conveying portion, and the part of the sample boat conveying portion is engaged with the guide rail and slides along the guide rail when the sample boat conveying portion moves up and down to thereby move the opening/closing cover in the horizontal direction.

2. The sample heating device according to claim 1, wherein a roller that can rotate in a vertical plane is provided to the part of the sample boat conveying portion to be engaged with the guide rail.

3. The sample heating device according to claim 2, wherein the guide rail is inclined in such a direction as to move the opening/closing cover toward a position above the opening of the mounting port according to the downward movement of the sample boat conveying portion and the sample heating device further comprises an opening/closing cover pushing portion that moves up and down with the sample boat conveying portion and pushes the opening/closing cover from above in synchronization with the downward movement of the sample boat conveying portion so that the opening/closing cover coming to the position above the opening of the mounting port to seal the opening.

4. The sample heating device according to claim 1, wherein the guide rail is inclined in such a direction as to move the opening/closing cover toward a position above the opening of the mounting port according to the downward movement of the sample boat conveying portion and the sample heating device further comprises an opening/closing cover pushing portion that moves up and down with the sample boat conveying portion and pushes the opening/closing cover from above in synchronization with the downward movement of the sample boat conveying portion so that the opening/closing cover coming to the position above the opening of the mounting port to seal the opening.

5. The sample heating device according to claim 1, wherein the sample boat conveying portion removes the sample boat from the sample boat rack, and mounts the sample boat to the mounting port after removing the sample boat from the sample boat rack.

* * * * *